United States Patent [19]

Kurz

[11] 4,204,548
[45] May 27, 1980

[54] SOUND FOR INSERTION IN THE BODY FOR THE DETERMINATION OF THE INTERNAL MEASUREMENTS OF HOLLOW ORGANS

[76] Inventor: Karl H. Kurz, Rheinbabenstrasse 5, Ecke Weissenbrugstrasse, 4000 Dusseldorf, Fed. Rep. of Germany

[21] Appl. No.: 906,972

[22] Filed: May 17, 1978

[30] Foreign Application Priority Data

Dec. 17, 1977 [DE] Fed. Rep. of Germany ....... 2756427
Dec. 17, 1977 [DE] Fed. Rep. of Germany ... 7738597[U]

[51] Int. Cl.² .............................................. A61B 5/10
[52] U.S. Cl. .................................................. 128/778
[58] Field of Search .................. 128/2 R, 2 S; 33/302, 33/125 B, 143 C, 174 D, 178 R, 178 E, 179

[56] References Cited

U.S. PATENT DOCUMENTS

| | | | |
|---|---|---|---|
| 2,223,000 | 11/1940 | Daley, Jr. | 33/179 |
| 2,241,451 | 5/1941 | Fist | 128/2 S |
| 2,725,486 | 11/1955 | Walstrom | 33/178 F |
| 4,016,867 | 4/1977 | King et al. | 128/2 S |

FOREIGN PATENT DOCUMENTS 69406 7/1914 Switzerland ............................... 33/179

Primary Examiner—William E. Kamm
Attorney, Agent, or Firm—Connolly and Hutz

[57] ABSTRACT

A sound or probe for determining the internal measurements of hollow organs and hollow parts of, for example, humans includes two rod shaped spring elements at the head of the sound which in turn are attached at their one end in an axial direction with their unattached ends spreading apart upon release of tension and with a thread under tensile stress connecting the spring elements and being guided to their base by the sound with means being provided for indicating the actual distance between the ends of the spring elements in accordance with the relative shifting position of the thread and sound.

9 Claims, 7 Drawing Figures

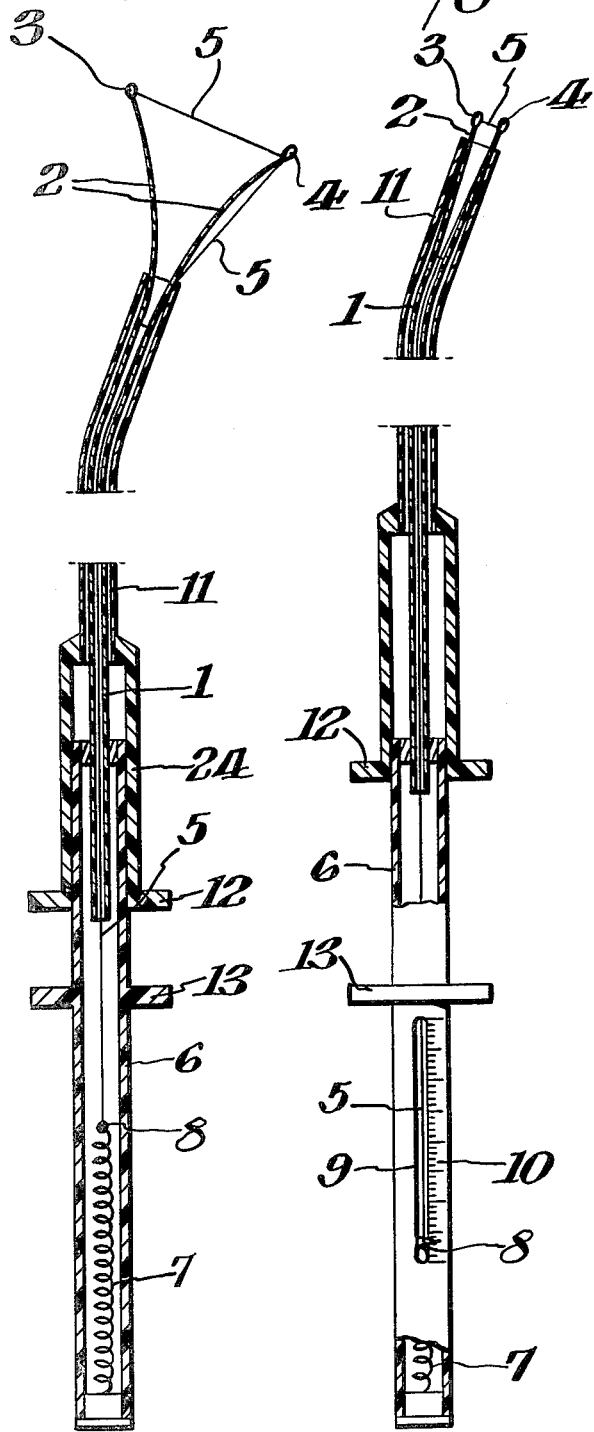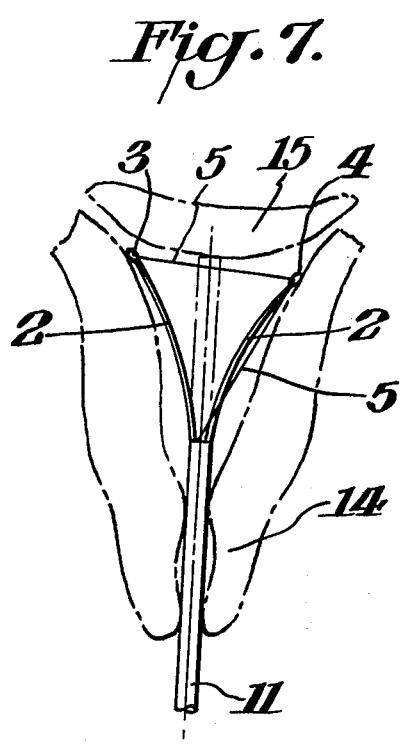

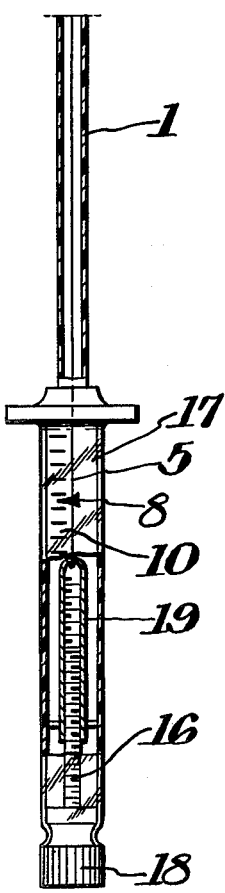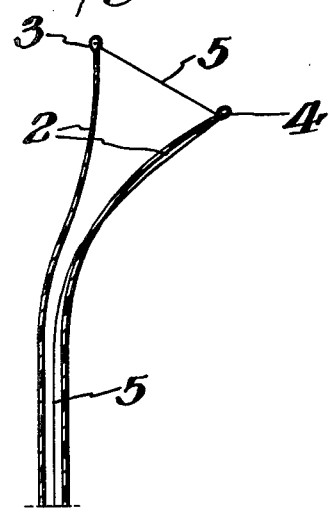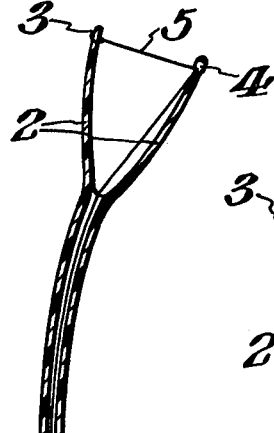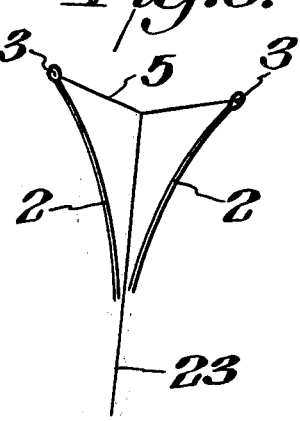

SOUND FOR INSERTION IN THE BODY FOR THE DETERMINATION OF THE INTERNAL MEASUREMENTS OF HOLLOW ORGANS

BACKGROUND OF THE INVENTION

The invention is concerned with a sound or probe for the determination of the internal measurements of hollow organs and hollow parts of the body, such as in a human, especially such which can only be reached by means of sounds which have a small cross-section, as for example, the uterine cavity.

The uterine cavity varies in size according to the individual, depending for example on age, the number of previous pregnancies and childbirths, and the intake of various hormonal preparations which are, for example, used for the treatment of dysfunctional bleeding, corpus luteum insufficiencies, endometriosis, uterine hypoplasia, myomas and also as oral contraceptives.

The measurement of the uterine cavity occurs thus far with the aid of sounds, the graduated scale of which makes it possible to determine the distance between the orifice of the uterus and the fundus, in the longitudinal direction. These sounds further serve to probe out the side walls of the uterus.

Other measures such as bi-manual palpation give a subjective estimate of the size and position of the organ. A contrast x-ray of the uterine cavity is possible with hysterosalpingography. This system is of limited use for genetic and fertility risk reasons.

The determination of changes in the interior of the uterus while under hormonal therapy, as for example, for the prevention of hypoplasia with resulting reduction in fertility, cannot be adequately performed by means of the described methods. The measurement of the uterine axis does not permit one to draw any conclusion regarding the overall change in the uterine cavity. The evaluation of this measure by itself can, in certain circumstances, lead to a false representation of the structure of the uterine cavity. The use of intra-uterine contraceptives or pessaries has shown a series of adverse effects, including metrorrhagia, endometritis, gradual perforations of the uterine wall, intracavity and ectopic pregnancies, as well as multiple laborlike contractions of the uterus which, based on experience, can be traced back to a dimensional incompatibility between the uterine cavity and the pessary. The measurement of the uterine cavity, especially the transverse measurement, i.e. the distance between both internal tubular os, is therefore a prerequisite for the use of fitted intrauterine pessaries.

SUMMARY OF THE INVENTION

The object of the invention is to achieve a sound for the determination of the internal measurements of hollow organs and hollow parts of the body which, aside from the determination of the longitudinal measurements, also permits a simple and exact determination of the transverse expansion or distention of the existing cavity.

This is attained, according to the invention, by means of two rod shaped spring elements at the head of the sound, which are, in turn, attached in an axial direction at one end with their unattached ends spreading apart from each other in one plane upon the release of tension. The invention also utilizes a thread, under tensile stress, connecting the rod shaped spring elements and being guided to their base by the sound. By means of the thread the acutal distance between the rod shaped spring elements is readable as the relative shift between sound and thread.

The thread can connect the rod shaped spring elements to one another at suitable opposing locations. Unless the special shape of the hollow organ to be measured does not allow this, the unattached ends are preferably connected with one another; since they assume the greatest possible distance with respect to one another, the relative shift between thread and sound thus becomes greatest.

The connection of the unattached ends of the rod shaped spring elements with the thread occurs most practically in such a way that the thread is attached to one end, while it is guided in sliding fashion in the other end and from there, extends to the base of the sound.

According to this type of attachment, the relative shift between sound and thread corresponds just about exactly to the actual distance between the unattached ends of the rod shaped spring elements.

A further possibility of connecting the unattached ends of the rod shaped spring elements consists of attaching the thread at both ends and to select the length of the thread such that it is at least nearly taut in the spread condition of the rod shaped spring elements. At the midpoint of the thread, an additional thread is attached and guided to the foot of the sound. With this type of connection, the relative shift between the thread and the sound does not have a linear relationship with the change in distance between the rod shaped spring elements. In the case of distance changes near the fully expanded state, there results a very great relative shift while in the case of distance changes near the stressed state, there results on the other hand only a very small relative shift. In the event that a reading scale is installed, it must therefore be non-linear. This type of connection for the unattached ends of the rod shaped spring elements if above all advantageous in such instances where there is a question of a very precise determination of the internal measurements of hollow organs having a diameter which nearly corresponds to the distance between the spread of the unattached ends of the rod shaped spring elements.

In all cases, it is best to pass the thread to the foot of the sound through a canal or passage inside the sound. Other guiding possibilities are, however, also applicable, e.g. guiding of the thread in its own guide tube or in guide loops mounted on the sound.

In practical use, the sound must be introduced into the cavity with the rod shaped spring elements in the taut condition after which the spring elements can be released inside the cavity. Various preferred designs of the inventive sound results, depending on how the stressing and relaxing of the rod shaped spring elements is effected.

This stressing and relaxing can be effected with the aid of a jacket in which the sound is installed so as to be shiftable. By pulling the head of the sound into this jacket, the rod shaped spring elements are tensed and finally drawn along into the jacket. The tensing of the thread can be brought about by means of a draw spring installed in a housing in the foot of the sound.

Since the diameter of the sound is somewhat increased as a result of the jacket, this arrangement presents problems in such applications where the entrance opening to the cavity is very narrow. In such cases, the force required for stressing the rod shaped spring elements is brought about by the thread itself in that it is tightened, for example, by a scroll installed at the foot of the sound. The thread can also be pulled directly by hand. This possibility is, above all, advantageous with those inventive sounds which are to be used as inexpensive one-way or single use devices. In this case, the sound and the rod shaped spring elements are advantageously made in one piece, out of plastic.

A reading scale is in all cases placed on the foot of the sound. If a housing for a worm drive or a draw spring is present, the housing can be provided with a slit at which the reading scale is located. A pointer attached to the thread projects through the slit and indicates the distance between the more or less spread apart unattached ends of the rod shaped spring elements. The fully relaxed position of the spring elements is established as the zero position. After the release of tension, the spring elements spread as far as the cavity in question permits. The degree of spreading and therewith the transverse measurement of the cavity is transmitted via the thread to the scale and can be read. Other designs are possible, however. For example, the housing can be transparent so that the relative shift of the thread and the sound can be observed in the interior of the housing insofar that an appropriate mark is placed on the thread. Finally, it is also possible, for special cases, to adapt the inventive sound insofar that only one rod shaped spring element is provided, its counterpart being a rigid rod.

All embodiments of the sound according to the invention allow a simple, rapid and precise determination of the internal measurements, of hollow organs and hollow parts of the body. Further advantages are evident from the examples of the invention hereinafter described.

THE DRAWINGS

FIG. 1 illustrates in cross-section a sound, in a jacket, in an almost completely tensed state;

FIG. 2 shows the sound according to FIG. 1, partly in section, in the almost completely relaxed state;

FIG. 3 shows a sound, according to which the tensile force is brought about by a worm drive;

FIG. 4 shows a sound designed as a single use device;

FIGS. 5 and 6 illustrate other embodiments of the thread connection of the rod shaped spring elements; and FIG. 7 shows a section of the uterine cavity with the introduced sound therein.

DETAILED DESCRIPTION

The embodiment according to FIGS. 1 and 2 consists of a hollow probe or sound 1, on the head of which, according to the invention, two rod shaped spring elements 2 are in turn attached at one end in an axial direction. The unattached ends of the rod shaped spring elements 2 can spread apart in one plane as illustrated in FIG. 2.

The unattached or free ends of the rod shaped spring elements 2 are equipped with rounded feelers 3, 4. To the feeler 3 is attached the end of a thread 5 which is passed through the feeler 4 in a slidable manner and which extends through the interior of the sound 1 to the latter's foot. A housing is mounted at the foot of the sound 1 with a draw spring 7 is attached to the end of the housing to keep the thread 5 taut.

A pointer 8 is attached to the thread 5 near the junction between the draw spring 7 and the thread 5 with pointer 8 being passed outward through a longitudinal slit 9 located in the housing 6. The longitudinal slit 9 is equipped with a scale 10. The thread 5 with the pointer 8 is pulled into the sound 1 under the force of the draw spring 7 the position thereof determining how far apart the rod shaped spring elements 2 are permitted to spread. The path covered by the pointer 8 is, for practical purposes, directly proportional to the actual spread of the free ends of the rod shaped spring elements 2. The transverse measurement of the existing cavity can therefore be read directly on the scale 10. When the rod shaped spring elements 2 are completely together, the pointer 8 assumes the zero position on the scale 10 similar to FIG. 1. By moving the sound 1 in an axial direction outwardly and by actual determination of the internal measurements, the structure of the inner space of the cavity in question can be ascertained, point for point, in one plane. If one turns the sound 1 about its axis, the measurements in another plane can be carried out so that in this manner one can finally measure the entire inner space, point for point.

The stressing and relaxing of the rod shaped spring elements 2 is effected by sliding the sound 1 in a jacket 11. The lower end of the jacket 11 is widened to form a housing 24 for taking up the housing 6 and ends in a grip ring 12. A corresponding grip ring 13 is placed on the housing 6. The grip rings 12, 13 serve to limit the sliding movement of the jacket 11 and allow one-handed manipulation of the device. When the jacket 11 slides downward toward the foot of the sound 1, the rod shaped spring elements 2 spread apart. Their spread becomes maximal when the grip rings 12 and 13 touch each other. In the upper end position, the rod shaped spring elements 2 are completely within the jacket 11. The opening of the jacket 11 is thereby sealed by the feelers 3 and 4 in such a way that no tissue injury can result from the introduction of the device into the cavity to be measured.

The functioning of the sound according to the invention is illustrated by means of FIG. 7 using the uterine cavity as an example:

The sound 1 is completely pulled into the jacket 11 before insertion so that the rod shaped spring elements 2 are located within the jacket 11 and so that feelers 3, 4 cover the opening of the jacket 11. The device is introduced, with this setting, through the orifice of the uterus 14 up to the fundus. This setting is indicated with dotted lines in FIG. 7. Without moving the sound 1 with the housing 6 the jacket 11 is now pulled back until the grip rings 12, 13 are next to each other. The rod shaped spring elements 2 thereby spread apart until the feelers 3, 4 are held by the interior wall of the uterus. Upon spreading of the rod shaped spring elements 2, the thread 5 is pulled under the force of the draw spring 7 into the foot of the sound. The path which is thereby covered can be read on the scale 10 by means of the pointer 8. The reading corresponds to the distance between the two feelers 3 and 4 and therefore also with the actual measurement of the inner space in a transverse direction.

Before withdrawing the device the jacket 11 is held firm and the sound 1 is pulled forward with the housing 6 until the rod shaped spring elements 2 are again inside the jacket 11. The device is then withdrawn.

Another embodiment of the sound according to the invention is shown in FIG. 3. The stressing and relaxing of the rod shaped spring elements is hereby effected by a worm drive 16 which is mounted in a housing 17 attached to the foot of the sound 1. The housing 17 is transparent so that the pointer 8 which is located on the thread 5 and which indicates on the scale 10 the measure of the spread of the rod shaped spring element 2 can be observed.

In the zero position of the pointer 8 the rod shaped spring elements 2 are held together by the thread 5. By turning the nut 18 the threaded spindle 19 is moved toward the foot of the sound 1 so that the rod shaped spring elements 2 can spread apart. As soon as the feelers 3 and 4 are held by the inner wall of the cavity, the pointer 8 stops since the connecting thread 5 is no longer under tension.

An additional advantageous design of the sound according to the invention is shown in FIG. 4. This design is especially suited as a one-way device or single use disposable device. The sound 1, the rod shaped spring elements 2, the feelers 3, 4 and the housing 20, located at the foot of the sound 1 are made in one piece from the same material, e.g. plastic. The eleasticity of the rod shaped spring elements 2 is thereby obtained through manufacturing steps. The thread 5 connects the rod shaped spring elements 2 as in the other designs and is attached to a rod 22, equipped with a scale 21, which is arranged so as to be slidable within the housing 20. The rod 22 projects partially from the housing 20. The measure of the projection of the rod 22 corresponds, in turn, to the spread of the rod shaped spring elements 2 and can be controlled by means of the scale 21.

When introducing the sound 1 into the cavity to be measured, the rod 22 is pulled back to its zero position so that the rod shaped spring elements 2 come together. As soon as the sound 1 is located in the desired position inside the cavity, the rod 22 is released so that the rod shaped spring elements 2 spread apart and come to rest against the inner wall of the cavity.

The distance of the feelers 3 and 4 from each other can then be read on the scale 21.

FIGS. 5 and 6 show a further possibility for the design of the thread connection. With the thread connection according to FIG. 5, the thread 5 is attached at the ends of both rod shaped spring elements 2 to the feelers 3 attached therewith. An additional thread 23 which leads to the foot of the sound 1 is fastened to the middle of the thread 5. The change in distance between the feelers 3 does not have, as was the case with the previous designs, a linear relationship with the shifting of the thread 23. The greater the distance between the feelers 3 becomes the greater the shifting of the thread 23 with a change in distance. An especially high measuring sensitivity is hereby obtained in the spread state of the rod shaped spring elements 2.

With the design according to FIG. 6, it is not the ends of the rod shaped spring elements which are connected by the thread 5. The connection occurs, rather, below the ends. This design is advantageous in such cases where the possibility of introducing the sound in an axial direction is limited but where the cavity continues sideways from the limitation.

What is claimed is:

1. A sound for the determination of the internal measurements of hollow organs and hollow parts of the body such as in humans, said sound comprising a longitudinal sound member having a head portion at one end thereof and a foot portion at the opposite end thereof, two rod shaped spring elements of generally uniform thickness disposed at said head portion, said spring elements being attached to said sound member at one end of said spring elements with the other end of said spring elements being unattached, a thread connected between said spring elements, tensioning means acting against said thread to resist said unattached ends of said spring elements spreading apart and to permit said unattached ends to spread apart in one plane upon release of tension therefrom, said sound member guiding said thread to the base of said spring elements, indicating means associated with said thread for indicating the actual distance between said unattached ends of said spring elements in accordance with the relative shift between said sound member and said thread, said sound member and said spring elements being slidably mounted in a jacket, and said jacket being of sufficient length that when said sound member is telescoped therein to its fully retracted position said sound member and said spring elements are completely within said jacket and thereby conform to the shape of said jacket without being exposed therefrom.

2. Sound according to claim 1, characterized therein that said thread is connected to said unattached ends of said rod shaped spring elements by being attached to one of the ends and passing through the other end in slidable fashion and extending therefrom to said foot portion of said sound member.

3. Sound according to claim 1, characterized therein that said sound member is hollow, and said thread passing through the interior of said sound member.

4. Sound according to claim 1, characterized therein that the tensile stress of said thread is brought about by a draw spring which is mounted in a housing attached to said foot portion of said sound member.

5. Sound according to claim 4, characterized therein that said housing is equipped with a longitudinal slit with a reading scale through which a pointer fastened onto the thread is passed to comprise said indicating means.

6. Sound according to claim 2, characterized therein that said sound member and said rod shaped spring elements are made in one piece out of plastic.

7. Sound according to claim 1 characterized therein that said foot portion of said sound member is designed as a housing in which a worm drive is connected to said thread for the application of tensile stress thereto.

8. Sound according to claim 7, characterized therein that said housing is equipped with a longitudinal slit with a reading scale through which a pointer fastened onto the thread is passed to comprise said indicating means.

9. Sound according to claim 3, characterized therein that said sound member and said rod shaped spring elements are made in one piece out of plastic.

* * * * *